(12) United States Patent
Kilian et al.

(10) Patent No.: US 8,753,879 B2
(45) Date of Patent: Jun. 17, 2014

(54) VCP-BASED VECTORS FOR ALGAL CELL TRANSFORMATION

(71) Applicants: Oliver Kilian, Los Altos, CA (US); Bertrand Vick, Berkeley, CA (US)

(72) Inventors: Oliver Kilian, Los Altos, CA (US); Bertrand Vick, Berkeley, CA (US)

(73) Assignee: Aurora Alage, Inc., Hayward, CA (US)

( * ) Notice: Subject to any disclaimer, the term of this patent is extended or adjusted under 35 U.S.C. 154(b) by 0 days.

(21) Appl. No.: 13/915,555

(22) Filed: Jun. 11, 2013

(65) Prior Publication Data

US 2013/0295665 A1     Nov. 7, 2013

Related U.S. Application Data

(63) Continuation of application No. 13/685,659, filed on Nov. 26, 2012, which is a continuation of application No. 12/480,635, filed on Jun. 8, 2009, now Pat. No. 8,318,482.

(60) Provisional application No. 61/059,672, filed on Jun. 6, 2008.

(51) Int. Cl.
*C12N 15/82* (2006.01)

(52) U.S. Cl.
USPC ..................................................... 435/320.1

(58) Field of Classification Search
None
See application file for complete search history.

(56) References Cited

U.S. PATENT DOCUMENTS

| | | | |
|---|---|---|---|
| 1,926,780 A | 9/1933 | Lippincott | |
| 3,468,057 A | 9/1969 | Buisson et al. | |
| 3,962,466 A | 6/1976 | Nakabayashi | |
| 4,003,337 A | 1/1977 | Moore | |
| 4,267,038 A | 5/1981 | Thompson | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,478,208 A | 12/1995 | Kasai et al. | |
| 5,527,456 A | 6/1996 | Jensen | |
| 5,661,017 A | 8/1997 | Dunahay et al. | |
| 5,668,298 A | 9/1997 | Waldron | |
| 5,723,595 A | 3/1998 | Thompson et al. | |
| 5,823,781 A | 10/1998 | Hitchcock et al. | |
| 6,027,900 A | 2/2000 | Allnutt et al. | |
| 6,117,313 A | 9/2000 | Goldman et al. | |
| 6,143,562 A | 11/2000 | Trulson et al. | |
| 6,166,231 A | 12/2000 | Hoeksema | |
| 6,297,054 B1 | 10/2001 | Maliga et al. | |
| 6,372,460 B1 | 4/2002 | Gladue et al. | |
| 6,448,055 B1 | 9/2002 | Shimizu et al. | |
| 6,736,572 B2 | 5/2004 | Geraghty | |
| 6,750,048 B2 | 6/2004 | Ruecker et al. | |
| 6,831,040 B1 | 12/2004 | Unkefer et al. | |
| 6,871,195 B2 | 3/2005 | Ryan et al. | |
| 7,244,609 B2 | 7/2007 | Drocourt et al. | |
| 7,381,326 B2 | 6/2008 | Haddas | |
| 7,410,637 B2 | 8/2008 | Sayre et al. | |
| 7,449,568 B2 | 11/2008 | Fukuda et al. | |
| 7,547,551 B2 | 6/2009 | Schuler et al. | |
| 8,039,230 B2 | 10/2011 | Otte et al. | |
| 8,119,859 B2 | 2/2012 | Vick et al. | |
| 8,314,228 B2 | 11/2012 | Kilian et al. | |
| 8,318,482 B2 | 11/2012 | Vick et al. | |
| 8,440,805 B2 | 5/2013 | Kilian et al. | |
| 2003/0049720 A1 | 3/2003 | Hoshino et al. | |
| 2003/0140021 A1 | 7/2003 | Ryan et al. | |
| 2003/0143743 A1 | 7/2003 | Schuler et al. | |
| 2003/0199490 A1 | 10/2003 | Antoni-Zimmermann et al. | |
| 2003/0211089 A1 | 11/2003 | Sayre et al. | |
| 2004/0161364 A1 | 8/2004 | Carlson | |
| 2004/0262219 A1 | 12/2004 | Jensen | |
| 2005/0064577 A1 | 3/2005 | Berzin | |
| 2005/0095569 A1 | 5/2005 | Franklin | |
| 2005/0124010 A1 | 6/2005 | Short et al. | |
| 2005/0170479 A1 | 8/2005 | Weaver et al. | |
| 2005/0181345 A1 | 8/2005 | Bradbury et al. | |
| 2005/0260553 A1 | 11/2005 | Berzin | |
| 2006/0031087 A1 | 2/2006 | Fox et al. | |
| 2006/0044259 A1 | 3/2006 | Hotelling et al. | |
| 2006/0045750 A1 | 3/2006 | Stiles | |
| 2006/0101535 A1 | 5/2006 | Forster et al. | |
| 2006/0122410 A1 | 6/2006 | Fichtali et al. | |
| 2006/0155558 A1 | 7/2006 | Corpening | |
| 2006/0166243 A1 | 7/2006 | Su et al. | |
| 2006/0166343 A1 | 7/2006 | Hankamer et al. | |

(Continued)

FOREIGN PATENT DOCUMENTS

| | | |
|---|---|---|
| CN | 1627764 | 6/2005 |
| CN | 1867140 | 11/2006 |

(Continued)

OTHER PUBLICATIONS

Sukenik et al (Journal of Phycology. Jun. 2000; 36(3): 563-570).*
Genbank Accession No. U71602 (*Nannochloropsis sp.* violaxanthin/chlorophyll a binding protein precursor (NANVCP) mRNA), 1998.*
In Journal37/2013, A1, Sep. 13, 2013, Vick et al.
Santin-Montanya, I. "Optimal Growth of *Dunaliella* Primolecta in Axenic Conditions to Assay Herbicides," Chemosphere, 66, Elsevier 2006, p. 1315-1322.
Felix, R. "Use of the cell wall-less alga *Dunaliella* bioculata in herbicide screening tests," Annals of Applied Biology, 113, 1988, pp. 55-60.

(Continued)

*Primary Examiner* — Scott Long
(74) *Attorney, Agent, or Firm* — Carr & Ferrell LLP (57) ABSTRACT

Provided herein are exemplary vectors for transforming algal cells. In exemplary embodiments, the vector comprises a Violaxanthin-chlorophyll a binding protein (Vcp) promoter driving expression of an antibiotic resistance gene in an algal cell. Embodiments of the invention may be used to introduce a gene (or genes) into the alga *Nannochloropsis*, such that the gene(s) are expressed and functional. This unprecedented ability to transform *Nannochloropsis* with high efficiency makes possible new developments in phycology, aquaculture and biofuels applications.

6 Claims, 8 Drawing Sheets

(56) References Cited

U.S. PATENT DOCUMENTS

| | | |
|---|---|---|
| 2006/0192690 A1 | 8/2006 | Philipp |
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0160488 A1 | 7/2008 | Younkes et al. |
| 2008/0160591 A1 | 7/2008 | Willson et al. |
| 2008/0194029 A1 | 8/2008 | Hegemann et al. |
| 2008/0268539 A1 | 10/2008 | Singh et al. |
| 2008/0293132 A1 | 11/2008 | Goldman et al. |
| 2009/0029445 A1 | 1/2009 | Eckelberry et al. |
| 2009/0061493 A1 | 3/2009 | Trimbur et al. |
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King et al. |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0107801 A1 | 5/2012 | Kilian et al. |
| 2012/0190115 A1 | 7/2012 | Kilian et al. |
| 2012/0208279 A1 | 8/2012 | Vick et al. |
| 2012/0277417 A1 | 11/2012 | Kilian et al. |
| 2012/0277418 A1 | 11/2012 | Kilian et al. |
| 2013/0078716 A1 | 3/2013 | Vick et al. |
| 2013/0102040 A1 | 4/2013 | Radakovits et al. |
| 2013/0131330 A1 | 5/2013 | Kilian et al. |
| 2013/0281683 A1 | 10/2013 | Kilian et al. |

FOREIGN PATENT DOCUMENTS

| | | |
|---|---|---|
| CN | 1956335 | 5/2007 |
| CN | 101289659 | 10/2008 |
| CN | 102164492 A1 | 8/2011 |
| CN | 102858980 A1 | 1/2013 |
| EP | 2297326 A1 | 3/2011 |
| EP | 2491124 A1 | 8/2012 |
| HK | 1175201 A1 | 6/2013 |
| MX | 20110000934 A1 | 7/2011 |
| WO | WO2004106238 A2 | 12/2004 |
| WO | WO2007084078 A1 | 7/2007 |
| WO | WO2008060571 A2 | 5/2008 |
| WO | WO2008106803 A1 | 9/2008 |
| WO | WO2008060571 A3 | 11/2008 |
| WO | WO2008060571 A8 | 2/2009 |
| WO | WO2009124070 A1 | 10/2009 |
| WO | WO2009149465 A1 | 12/2009 |
| WO | WO2009149470 A1 | 12/2009 |
| WO | WO2010011335 A1 | 1/2010 |
| WO | WO2010147662 A1 | 12/2010 |
| WO | WO2011011463 A2 | 1/2011 |
| WO | WO2011049995 A1 | 4/2011 |
| WO | WO2012149457 A1 | 11/2012 |
| WO | WO2013166065 A1 | 11/2013 |

OTHER PUBLICATIONS

Janssen, M. "Phytosynthetic efficiency of *Dunaliella* tertiolecta under short light/dark cycles," Enzyme and Microbial Technology, 29, 2001, p. 298-305.

Saenz, M.E., "Effects of Technical Grade and a Commercial Formulation of Glyphosate on Algal Population Growth," Bulletin of Environmental Contamination Toxicology, 1997, 59: pates 638-644.

Christy et al., "Effects of Glyphosate on Growth of *Chlorella*," Weed Science, vol. 29, Issue 1, Jan. 1981, pp. 5-7.

Roessler et al., "Genetic Engineering Approaches for Enhanced Production of Biodiesel Fuel from Microalgae," ACS Symposium Series; American Chemical Society, 1994, pp. 255-270.

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601.

In Journal31/2013, A1, Aug. 2, 2013, Kilian et al.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of Chlamydomonas Using the Chlamydomonas Gene for Nitrate Reductase" The Journal of Cell Biology 109 (6, part 1): 2589-2601.

Prein et al. "A Novel Strategy for Constructing N-Terminal Chromosomal Fusions to Green Fluorescent Protein in the Yeast *Saccharomyces cerevisiae*" FEBS Letters 485 (2000) 29-34.

Schiedlmeier et al., "Nuclear Transformation of Volvox Carteri" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla Chlamydomonas reinhardtii," Plant Jour. ePub Jan. 17, 2009, vol. 58, No. 1, pp. 157-164 (Abstract Only).

Chen et al., "Conditional Production of a Functional Fish Growth Hormone in the Transgenic Line of *Nannochloropsis* oculata (Eustigmatophyceae)," J. Phycol. Jun. 2008, vol. 44, No. 3, pp. 768-776.

Nelson et al., "Targeted Disruption of NIT8 Gene in Chlamydomonas reinhardtii." Mol. Cell. Bio. Oct. 1995, vol. 15, No. 10, pp. 5762-5769.

Kureshy et al., "Effect of Ozone Treatment on Cultures of *Nannochloropsis* oculata, Isochrysis galbana, and Chaetoceros gracilis," Journal of the World Aquaculture Society, 1999, 30(4), pp. 473-480.

Abe et al., AG610981, Musmusculus molossinus DNA, 2004.

Kopczynski et al., CO268749, Drosophila melanogaster cDNA clone EK092604, 2004.

Csogor et al., "Light Distribution in a Novel Photobioreactor -Modelling for Optimization," Journal of Applied Phycology, vol. 13, pp. 325-333.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis Sp*. In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga *Nannochloropsis* Oculata (eustigmatophyceae)," Journal of Phycol, vol. 44, pp. 99-102, 2008.

Thiel et al., "Transformation of a Filamentous Cyanobacterium by Electroporation," Journal of Bacteriology, Oct. 1989, vol. 171, No. 10, pp. 5743-5746.

Krienitz et al., "*Nannochloropsis* limnetica (Eustigmatophyceae), a new species of picoplankton from freshwater," Phycologia, 2000, vol. 39, No. 3, Abstract.

Lee et al., "Isolation and Characterization of a Xanthophyll Aberrant Mutant of the Green Alga *Nannochloropsis* oculata," Marine Biotechnology, 2006, vol. 8, pp. 238-245.

Sukenik et al., "Regulation of Fatty Acid Composition by Irradiance Level in the Eustigmatophyte *Nannochloropsis*," Journal of Phycol., 1989, vol. 25, pp. 686-692.

Rocha et al., "Growth Aspects of the Marine Microalga *Nannochlorpsis* gaditana," Biomolecular Engineering, 2003, vol. 20, pp. 237-242.

(56) References Cited

OTHER PUBLICATIONS

MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.
Dunahay et al, "Manipulation of Microalgal Lipid Production Using Genetic Engineering," Applied Biochemistry and Biotechnology, 1996, vol. 57/58/.
Witkowski et al., "Conversion of a B-Ketoacyl Synthase to a Malonyl Decarboxylase by Replacement of the Active-Site Cysteine with Glutamine," Biochemistry, 1999, vol. 38, 11643-11650.
Kisselev, "Polypeptide Release Factors in Prokaryotes and Eukaryotes: Same Function, Different Structure," Structure, vol. 10, Jan. 2002.
Whisstock et al., "Predication of protein function from protein sequence and structure," Q. Rev. Biophysics, 2003, vol. 36, pp. 307-340.
Broun et al., "Catalytic Plasticity of Fatty Acid Modification Enzymes Underlying Chemical Diversity of Plant Lipids," Science, vol. 282, 1998.
Wishart et al., "A Single Mutation Converts a Novel Phosphotyrosine Binding Domain into a Dual-specificity Phosphatase," J. Biol. Chem. 1995, vol. 270(45), pp. 26782-26785.
Geng et al, "Construction of a System for the Stable Expression of Foreign Genes in *Dunaliella salina*," Acta Botanica Sinica 46(3): 342-346, 2004.
Chen et al., "Highly Efficient Expression of Rabbit Neutrophil Peptide-1 gene in Chlorella Ellipsoidea Cells," Current Genetics 39(5-6): 365-370, 2001.
Suga et al., "Control by Osmolarity and Electric Field Strength of Electro-Induced Gene Transfer and Protein Release in Fission Yeast Cells," Journal of Electrostatics 64(12): 796-801, 2006.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)-Communications and Administration Office, Apr. 2008.
Department of Environment, Housing and Territorial Development Ministry, Resolution (1009), published Jun. 17, 2008.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25, 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, Cyanidioschyzon merolae 10D," Plant and Cell Physiology, vol. 45, No. 6, Jun. 2004, pp. 667-671.
Hallmann et al., "Gene Replacement by Homologous Recombination in the Multicellular Green Alga, Volvox carteri," Proceedings of the National Academy of Sciences in the United States of America, vol. 94, No. 14, 1997, pp. 7469-7474.

Kilian et al., "High-efficiency homologous recombination in the oil-producing alga *Nannochloropsis sp.*," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of Chlamydomonas Reinhardtll," Created Dec. 2003, [online, retrieved Oct. 14, 2010] <http://etd.Isu.edu/docs/available/etd-0828103-114026/unrestricted/Pollock_dis.pdf>.
DROCOURT: GenBank Accession No: X52869.1, created Jan. 3, 1995.
PAN: GenBank Accession No: EE109892.1, created Jun. 23, 2008.
PAN: GenBank Accession No: EE109907, created Jun. 23, 2008.
Henriquez et al.: GenBank Accession No: Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of *Nannochloropsis* oculata (Eustigmatophyceae)," Chinese Journal of Oceanology and Limnology, vol. 28, No. 4, pp. 802-807, 2010.
Lumbreras et al., "Efficient Foreign Gene Expression in Chlamydomonas Reinhardtii Mediated by an Endogenous Intron," The Plant Journal, vol. 14, No. 4 Jan. 1, 1998, pp. 441-447, XP001150496, ISN: 0960-7412, DOI: 10.1046/j.1365-313X.1998.00145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in Arabidopsis," The Plant Journal, vol. 40, No. 5, Dec. 1, 2004, pp. 744-751, XP55029911, ISSN: 0960-7412, DOI:10.1111/j.1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.
Examination Report mailed Feb. 20, 2013 in Australian Application No. 2009274500 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.X filed Jul. 24, 2009.
Zuo-Xi Ruan et al., Effects of Acute Glyphosate Exposure on the Growth and Physiology of Nostoc Sphaeroides, an Edible Cyanobacterium of Paddy Rice Fields, Acta Hydrobiologica Sinica, Jul. 2008 vol. 32, No. 4.
Office Action mailed Nov. 11, 2013 in Mexican Application No. MX/a/2011/000934 filed Jul. 24, 2009.

* cited by examiner

FIGS. 1A-1B

```
GGCGGTCTTTTGTCTTCCTCTATAGCCCGCCCGTCTAGAGGGCACACGGCGATGATCTTTATATCTCTTC
ATGTCTCTTTGTTTAACTAGGATACTGCCGGGTGAATGCCCATCGGACAAGAGCCAAACTCTATCTACAC
CCTTTTGACTTCTGTTGTGTCGTAGTGTGTCGTTGCATGCCCTGAAAGTCCAGGCATCCCACTGTGCTCTA
ACCCCATTCAAAACAGCAGAAGTGCTTAATTAAGATATAGATTCATGATCTCCTGTCCCCTCCTTCTTACCT
TTTCACAAACCTCACACAGAAGTCTCCACTCTTCGCCTCTAAAACCTCTTTTTAAATT
ATGGTAAGTTCGTGCGGCAGTGGGTTTCGGATCTATATTTGTCAAGATCAGTTCAAGGTCAGGGAT
GTAGATTAAGTACAGAAGGAGAAGCACAAGCGGCCAGTTCGCCCCTCACGGCCTGGAGCAGGGCATTT
AATCCCTCTATCTTACCAGAACCATATACAACCAATCCTGTTGGCATCGCTCTGTCTATTTGTCGT
GCCTGCATGTCTCCATGCTGTGGGGGCAGGGTTTCGGGGTTGCGGTTGAAGGCACCTTATCA
GAAAGATGCCCTCAGAGATAGAGGTAGCCCCTCCCCCGATCTTCGACCAGTCCTGCAGGGAACACT
TTCACCCGTCGTTCACCTCGTTACACACAAGGAGTAGAACCTCTGAAGTTCTAATTGTCATAAATGCCCC
TCCCCCCTCCCTCTTTCCCTTGATCCTCCCCCTCCGAGCAGATT ATG
GCCAAGTTGACCAGTGCCGTTCCGGTGCCTCACCGCGCGACGTCGCCGGAGCGGTCGAGTTCTGGACC
GACCGGTCGGGTTCCGGGTCAGGACCAGGTTCGTGAGGACGACTTCGCCGGTCGCCGGACGACGTGACC
CTGTTCATCAGCCGGTCCAGGACCAGGTTGTCGCGGACAACACCCTGGCCTGGTGTGGCTGCGGGAC
CTGGACGAGCTGTACGCCCAGCTGGTCGCGAGCTGCTTCCACGAACTTCCCGGACCGCCTCCGGCCCGCC
ATGACCGAGATCGGCGAGCAGCCCTGGGGCGCCGAGTTCGCCTGCGACCCGGCCCGGCAACTGCGTG
CACTTCGTGCCCGAGGAGGAGCAGGACTAA
GCTTCTGTGGAAGAGCCAGTGGTAGTAGCAGTAGCAGCCGCAGCACTCAGTGTTGGC
GCGAGAGATTGTCCATCCCTTCTTAACCTACCGGAAGAGAAATAAGGCCTTTCTCCGTAGCTGTCTTC
GTTTGTTTGTGCTGATTGCTTGATATGAGAGTGTTGAATTCCTGCATCATGTTTTCTCTGTAGTCCT
TTCCTACCCCGTCATTTCTTTCTTCCCGGTTCTTTGTCACCCTTATTTACATAAAAATTTC
TTTGTTTATAGTGAGAGGAAGGTAGAGAGGGAAAACAAGAACAAGAACGCAAGCGTGTGAAAGGA
GGGCGACTAGAAGAGAAACAGATCTGTTGAGCATTGAGAGTGAGCGGGGAAAGGCTTGTGTGTTG
TCTTTGAAAAAGTGTTTTAAATCACGAATCCGTTAGTTCTCATGTTCTCATGTTACCCTCTTTGTTACTACTGTGAT
GGAGAAAACAAAAGTGTGAGGATTAATTGAAGAAAAGAAGAGTTCGACACGTCAAACCGCCAAAAG
ACGTCACAAAGAGAAACTTGATTCTCTTTGCCGTGTTGATCCTGTCTTTTCCCCCAGCTTTTCTTGCCACCGT
GGCACaCGGAGAtTGgACAAGATCAg
```

FIG. 2

```
GGCGGTCTTTTGTCCTTTTCCTCTATAGCCCGCCCCGTCTAGAGGGCACACGCGATGATCTTTATATCTCTTCATGTGTCTTTGTTTT
AACTAGGATACTGCCGGGTGAATGCCCATCGGACAAGAGCCAAACTCTATCTACACCCTTTTGACTTCTGTTGTGGTCGTAGTGTG
TGCTTGCATGCCCTGAAAGTCCAGGCATCCCACTTGTGTCTCTAACCAGTCATTCAAAAACAGCAGAAGTGCTTAATTAAGATATATA
ATGATCTCCTGTCCCCTCCTTCTTACCTTTTCACAAACTCACACAGAAGTCTTCGCCTCTAAAACCTCTTTTTAAATT

ATGGTAAGTTCGTGCGGGCAGTGGGTTTCGGGATCTATATTTGTCAAGATCCAGTTCAAGGTTCAGGGATGTAGATTAAGTACA
GAAGGAGAAGCACAAGCCGCGCCAGTTCGCCCCTCAGGCCTGGAGCCAGGGCATTTAATCCCTCTATCTTACCAGAACCATACTA
TACAACCAATCCTGTGGCATCGCTCTGTCTATTTGTCGTGCTGCATGTGTCCATGGTGTGTGCCCCTCGGGGGGCAGGGGTTTCGG
GGTTGCGGTTGAAGGCACCTTATCAGAAAGATGCCTCAGAGATAGAGGTAGGCCCCTCCCCGATCTTCGACCAGTCCTGTC
AGGCGAACACTTTCACCCGTCGTTCACCTCGTTACACACAAGGAGTAGACCTCTGAAGTTCTAATTGTCATAAATGCCCCTCCC
CCCTTCCCCTCTTTCCCTTGATCCTCCCCCTGAGCAGATTATG

AAGAAACCTGAACTGACAGCAACTTCTGTTGAGAAGTTTCTCATTGAAAATTTGATTCTGTTTCTGATCTCATGCAGCTGTC
TGAAGGTGAAGAAGCAGAGCCTTTCTTTCTTTGATGTTGGAGGAAGGTTATGTTCTGAGGGTCAATTCTTGTCTGATGGT
TTTACAAAGACAGATATGTTTACAGACACTTGCCCTCTGCCTCACTCTCAGAAGTTCTGGACATTGGAGAATTTTC
TGAATCTCTCACCTACTGCATCAGCAGAAGAGCACAAGGAGTCACTCTCCCTGAAACTGAGCTGCCAGCTGTTCT
GCAACTGTTGCTAGTACACCACTTGGAAGTGATGCCATTGCAGCAGTCTGATCCTCGAGCGAAACTCTGGATTTGGTCCTTTGGTCCAAG
GCATTGGTCAGTACACCACTTGGAGGGATTTCATTTGTCGAGGCACTGTAACTGGCAGATTGTCCTGAAGTCAGACACCTGGT
GACACAGTTTCTGCTTCTGTTGCTGAAGCAACAATTGGCACTCTGACAGAATGGCCAGTCACTGCAGTCATTGACTGCTCTGAAGCCATGCTTTG
CCATTCGGATTTTGGAAGCAACAATATTTTTGGAGACCTTGGCTGCTCATGCATGTGAGACCAACAACAAAGATATTTGA
AAGAAGACACCCAGAGTCAGGTTGCCAATCTGAGAACTGGCTGTGCTGACCAACTGTATCAATCTC
TGGTTGATGGAAACTTTGATGCTGCATTGTTTGGGCACAGAAGATGTGATGGATGTGTTGAAGTTCTGCTGTGGGAACTGTTGG
AAGAACTCAAATTGCAAGAAGGTTCTGCTGCTGTTTGGACTGATGATGGTGTTGAAGTTCTGCTGACTCTGGAAACAGGAGA
CCCTCCACAAGACCCAGCCAAGGAATAA

GCTTCTGTGGAAGAGCCAGTGGTAGTAGCAGTAGCAGCAGCCCGAGCAGCACTCAGTGTTGGCCGAGATTGTCC
ATCCCTTCTAACCTACCGGAAGAGAAATAAGGCCTTTCTCCCGTAGCTGTCTTCGTTGTTGTGCTGATTGCTTGATATGA
GAGTGTTGAATTCCTGCATCATGTTTTCTCTGTAGTCATGTTTATAGTGAGAGAAGTAGAGGGCAGAAACAAGCAACGAAGCG
CACCCTTATTTATACATAAAATTTTCTTGTTTATAGTGAGAAACAGATCTGTTAGCATTGAGCAGTTGGGGGAAAAGGCTTGTGTCTT
TGTGAAAAAGTTGTTTAAATCACGAATCCGTTAGTTCTGTAGTCCTCTTTCACTACATGTGATGAGAACAAACAAAGTGTG
AGGATTAATTGAAGAAAAAGAAGAGTTGAACACGTTCAAACCGCCCAAAAGACGTTCACAAGAACTTGATTCTCTTGTTCCGTGT
TGATCCTGTCTCTTTCCCCAGCTTTTTCTGCCACCCGTGGCACaCGGACGAGATGgACAAGATCAg
```

FIG. 3

```
GGCGGTCTTTGTCCTTTCCTCTATAGCCCGCCCCTCAGAGGGCACACGCGATGATCTTTATATCTCTTCATGTGTCTTT
GTTTAACTAGGATACTGCGCGGTGAATGCCATCGGACAAGAGGCCAAACTCTATCTACACCCTTTGACTTCTGTGG
TCGTAGTGTGTGCTTGCATGCCCTGAAAGTCCAGGCATCCCACTTGTCTCTAACCCATTCAAAACAGCAGAAGTGCTTAA
TTAAGATATAGATTCATGATCTCCTGTCCCCTTCCTTCTTACCTTTTCACAAACCTCACACAGAAGTCTCCACTCTTCGCCTC
TAAAACCTCTCTTTTAAATT
ATGGTAAGTTCGTCGCGGCAGTGGGTTTTCGGATCTATATTTGTCAAGATCCAGTTCAAGGTCAGGGATGTAGATTAA
GTACAGAAGGAGAAGCACAAGGCGGCCAGTTCGCCCCTCACGGCCTGAGCAGGGCATTTAATCCCTCTATCTTACCA
GAACCATACTATACAACCAATCCTGTTGCGGTTGCGGTTGAAGGCACCTTATCAGAAAGATGCCCTCAGAGATAGAGGTAGCCCCTCCC
GGGCAGGGGTTTTCGCGGTTGCGGTTGAAGGCACCTTTCACCCTCTTCCCTCTTGATCCTCCCGAGCAGATT
CCGATCTTCGACCAGTCCTGTCAGCGAACACTTTCACCCTCGTTACACACAAGGAGTAGACCTCTGAA
GTTCTAATTGTCATAAATGCCCCTCCCCCCTTCCCTCTTGATCCTCCCGAGCAGATT
ATGAAGACCTTCAACATCTCTCAGCAGGATCTGGAGCTGGTCGCCACTGAGAAGATCACCATGCTCTATGAG
GACAACAAGCACCATGTCGGGGCGGCCATTAAGGACCAAGACTGGGGAGATCATCTCTGCTGTCCACATTGAGGCCTAC
ATTGGCAGGTCACTGTCTGTCAGGCACCCCTACTCTGATGAGTGGACAGATCCATCAGGGTGGTCAGCCCTGGGCATGTGCAGA
ATTGTGGCTTCAGGCACCCCTACTCTGATGAGTGGACAGATCCATCAGGGTGGTCAGCCCTGGGCATGTGCAGA
GAGTCATCTCTGACTATGCCTCCCTGACTGCTTTGTGCTCATTGAGATGAATGGCAAGCTGGTCAAAACCACCATTGAG
GAACTCATCATCCCCCCTCAAGTAGTACACCAGGAACTAA
GCTTCTGTGAAGAGCCAGTGGTAGTAGCAGTAGCAGTAGCAGCCGCAGCAGCACTCAGTGTTGGGCGGAGAGAT
TGTCCATCCCTTCTTAACCTACGGAAGAGAAATAAGGCCTTTCTCCGTAGCTTCGTTTGTTTGTGCTGATTG
CTTGATATGAAGAGTGTTGAATTCCTGCATCATGTTTCTCGTAGTTCTTTGTTTATAGTGACAGGAAGTGAGAGGGGAAAA
CAAGAACAACCAACCAAGCTTGTCTGTGAAAGAGCAGAGCAGTAGAAGAGAAAATCGTTAGTTCTTCTAGTGTACCTCTTT
CGGGGAAAGGCTTGTGTGTCTTGAGAAACAAAAGTGTGAGGATTAAATTGAAGAAAAAGAAGAGTTCGACACGTCAAACCGCCA
CACTACATGTGATGGAGAAAGAGAACTTGATTCTCTTTCGCGTGTTGATCCGTGTCTCTTTTCCCCAGCTTTCTTTTGCCACCCGTGGACA
AAGACGTCACAAAGAGAACTTGATTCTCTTTCGCGTGTTGATCCGTGTCTCTTTTCCCCAGCTTTCTTTTGCCACCCGTGGACA
CGAGATGgACAAGATCAg
```

802 {
TGNGGAATTTTCCAGATGAAGTATCATCTAAGAATTTAAATGAAGAAGACTTCAGAGCTTTTGTTAAAAA
TTATTTGGCAAAAATAATATAATTCGAATTCACGTGT

804 {
GTGGCATGGGCAACGGTATCTCGTCCAGACGATGCAGCGGGAATGTCCGCAAAAGGTTGGTTTATTTTAAG
GACACATCTTATCAACTAATGAAAGCTTGGGCCTCCGTTTGTGCTTCTGGAATGGGACTGAATGCTGCTGC
CGTAGCTGCTGCTGCTGCTGCTCAGCAGCAATGGCGTGAAAAGGATGCCTCCCATCTCCTTGTCTTTCCTG
ACACCACCTCCCCATAAATCTCAACCAATACAGCACCCAGGCTTCCATCAAGTGGCGGTGGGTTGAAGAAA
CGCATTGATACTCGCTTGCGTGCTTGGTGCTATCCAGGAAANAAAAAAANNN

FIG. 8

SEQUENCE LISTING

<160> NUMBER OF SEQ ID NOS: 3

<210> SEQ ID NO 1
<211> LENGTH: 1820
<212> TYPE: DNA
<213> ORGANISM: Nannochloropsis

<400> SEQUENCE: 1

```
ggcggtcttt tgtcctttcc tctatagccc gcccgtctag agggcacacg cgatgatctt      60
tatatctctt catgtgtctt tgttttaact aggatactgc cgggtgaatg cccatcggac     120
aagaggccaa actctatcta caccctttg acttctgttg tggtcgtagt gtgtgcttgc     180
atgccctgaa agtccaggca tcccacttgt gctctaaccc cattcaaaac agcagaagtg     240
cttaattaag atatagattc atgatctcct gtcccctcct tcttaccttt tcacaaacct     300
cacacagaag tctccactct tcgcctctaa aacctctttt taaattatgg taagttcgtg     360
cggcagtggg ttttcggatc tatatttgtc aagatccagt tcaaggtcag ggatgtagat     420
taagtacaga aggagaagca caagcgcgcc agttcgcccc tcacggcctg gagcagggca     480
tttaatccct ctatcttacc agaaccatac tatacaacca atcctgttgg catcgctctg     540
tctatttgtc gtgcgtgcat gtgtccatgg tgtggtgggg ggcagggggtt ttcggggttg     600
```

```
cggttgaagg caccttatca gaaagatgcc ctcagagata gaggtagccc cctcccccg      660 atcttcgacc agtcctgtca ggcgaacact ttcacccgtc gttcacctcg ttacacacaa     720
ggagtagacc tctgaagttc taattgtcat aaatgcccct ccccctccc tctttccctt      780 gatcctcccc tccgagcaga ttatggccaa gttgaccagt gccgttccgg tgctcaccgc     840
gcgcgacgtc gccggagcgg tcgagttctg gaccgaccgg ctcgggttct cccgggactt    900
cgtggaggac gacttcgccg gtgtggtccg gacgacgtg accctgttca tcagcgcggt      960
ccaggaccag gtggtgccgg acaacaccct ggcctgggtg tgggtgcgcg gcctggacga    1020
gctgtacgcc gagtggtcgg aggtcgtgtc cacgaacttc cgggacgcct ccgggccggc    1080
catgaccgag atcggcgagc agccgtgggg gcgggagttc gccctgcgcg acccggccgg    1140
caactgcgtg cacttcgtgg ccgaggagca ggactaagct tctgtggaag agccagtggt    1200
agtagcagta gcagcagcag tagcagccgc agcactcagt gttggcgcga gagattgtcc    1260
atcccttctt aacctaccgg aagagaaata aggcctttct cccgtagctg tcttcgtttg    1320
tttgtgctga ttgcttgata tgagagtgtt gaattcctgc atcatgtttt tctctgtagt    1380
cctttcctac ccccgtcatt ttcttttctc cctggttctt cttttgtcac ccttatttta    1440 cataaattt tctttgttta tagtgagagg aaggtagaga ggggaaaaca agaacaacga    1500
acgcaagcgt gtgaaaggag ggcgagtaga agagaaacag atctgttgag cattgagagt    1560
ggagccgggg gaaaggcttg tgtgttgtct ttgaaaaagt tgtttaaatc acgaatccgt    1620
tagttctcat gtgtacctct ttcactacat gtgatggaga aaacaaaagt gtgaggatta    1680
attgaagaaa aagaagagtt cgacacgtca aaccgcccaa aagacgtcac aaagagaact    1740
tgattctctt tgccgtgttg atcctgtctt ttccccagc ttttcttgcc acccgtggca    1800
cacgagatgg acaagatcag                                               1820

<210> SEQ ID NO 2
<211> LENGTH: 2471
<212> TYPE: DNA
<213> ORGANISM: Nannochloropsis

<400> SEQUENCE: 2
ggcggtcttt tgtcctttcc tctatagccc gcccgtctag agggcacacg cgatgatctt     60
tatatctctt catgtgtctt tgttttaact aggatactgc cgggtgaatg cccatcggac    120
aagaggccaa actctatcta caccttttg acttctgttg tggtcgtagt gtgtgcttgc    180
atgccctgaa agtccaggca tcccacttgt gctctaaccc cattcaaaac agcagaagtg    240
cttaattaag atatagattc atgatctcct gtcccctcct tcttaccttt tcacaaacct    300
cacacagaag tctccactct tcgcctctaa aacctctttt taaattatgg taagttcgtg    360
cggcagtggg ttttcggatc tatatttgtc aagatccagt tcaaggtcag ggatgtagat    420
taagtacaga aggagaagca caagcgcgcc agttcgcccc tcacggcctg agcagggca    480 tttaatccct ctatcttacc agaaccatac tatacaacca atcctgttgg catcgctctg    540
tctatttgtc gtgcgtgcat gtgtccatgg tgtggtgggg ggcagggttt tcggggttg    600 cggttgaagg caccttatca gaaagatgcc ctcagagata gaggtagccc cctcccccg    660 atcttcgacc agtcctgtca ggcgaacact ttcacccgtc gttcacctcg ttacacacaa     720
ggagtagacc tctgaagttc taattgtcat aaatgcccct ccccctccc tctttccctt      780 gatcctcccc tccgagcaga ttatgaagaa acctgaactg acagcaactt ctgttgagaa    840
gtttctcatt gaaaaatttg attctgtttc tgatctcatg cagctgtctg aaggtgaaga    900
```

```
aagcagagcc ttttcttttg atgttggagg aagaggttat gttctgaggg tcaattcttg    960
tgctgatggt ttttacaaag acagatatgt ttacagacac tttgcctctg ctgctctgcc   1020
aattccagaa gttctggaca ttggagaatt ttctgaatct ctcacctact gcatcagcag   1080
aagagcacaa ggagtcactc tccaggatct ccctgaaact gagctgccag ctgttctgca   1140
acctgttgct gaagcaatgg atgccattgc agcagctgat ctgagccaaa cctctggatt   1200
tggtcctttt ggtccccaag gcattggtca gtacaccact tggagggatt tcatttgtgc   1260
cattgctgat cctcatgtct atcactggca gactgtgatg gatgacacag tttctgcttc   1320
tgttgctcag gcactggatg aactcatgct gtgggcagaa gattgtcctg aagtcagaca   1380
cctggtccat gctgattttg gaagcaacaa tgttctgaca gacaatggca gaatcactgc   1440
agtcattgac tggtctgaag ccatgttttgg agattctcaa tatgaggttg ccaacatttt   1500
tttttggaga ccttggctgg cttgcatgga acaacaaaca agatattttg aaagaagaca   1560
cccagaactg gctggttccc ccagactgag agcctacatg ctcagaattg cctggaccaa   1620
actgtatcaa tctctggttg atggaaactt tgatgatgct gcttgggcac aaggaagatg   1680
tgatgccatt gtgaggtctg gtgctggaac tgttggaaga actcaaattg caagaaggtc   1740
tgctgctgtt tggactgatg gatgtgttga agttctggct gactctggaa acaggagacc   1800
ctccacaaga cccagagcca aggaataagc ttctgtggaa gagccagtgg tagtagcagt   1860
agcagcagca gtagcagccg cagcactcag tgttggcgcg agagattgtc catcccttct   1920
taacctaccg gaagagaaat aaggcctttc tcccgtagct gtcttcgttt gtttgtgctg   1980
attgcttgat atgagagtgt tgaattcctg catcatgttt ttctctgtag tccttttccta   2040 cccccgtcat tttctttttct ccctggttct tcttttgtca cccttatttt acataaaatt   2100
ttctttgttt atagtgagag gaaggtagag agggaaaac aagaacaacg aacgcaagcg   2160
tgtgaaagga gggcgagtag aagagaaaca gatctgttga gcattgagag tggagccggg   2220
ggaaaggctt gtgtgttgtc tttgaaaaag ttgtttaaat cacgaatccg ttagttctca   2280
tgtgtacctc tttcactaca tgtgatggag aaaacaaaag tgtgaggatt aattgaagaa   2340
aaagaagagt tcgacacgtc aaaccgccca aaagacgtca caaagagaac ttgattctct   2400
ttgccgtgtt gatcctgtct tttcccccag cttttcttgc cacccgtggc acacgagatg   2460
gacaagatca g                                                        2471
```

<210> SEQ ID NO 3
<211> LENGTH: 1868
<212> TYPE: DNA
<213> ORGANISM: Nannochloropsis

<400> SEQUENCE: 3

```
ggcggtcttt tgtcctttcc tctatagccc gcccgtctag agggcacacg cgatgatctt     60
tatatctctt catgtgtctt tgttttaact aggatactgc cgggtgaatg cccatcggac    120
aagaggccaa actctatcta caccctttttg acttctgttg tggtcgtagt gtgtgcttgc    180
atgccctgaa agtccaggca tcccacttgt gctctaaccc cattcaaaac agcagaagtg    240
cttaattaag atatagattc atgatctcct gtcccctcct tcttaccttt tcacaaacct    300
cacacagaag tctccactct tcgcctctaa aacctctttt taaattatgg taagttcgtg    360
cggcagtggg ttttcggatc tatatttgtc aagatccagt tcaaggtcag ggatgtagat    420
taagtacaga aggagaagca caagcgcgcc agttcgcccc tcacggcctg gagcagggca    480
tttaatccct ctatcttacc agaaccatac tatacaacca atcctgttgg catcgctctg    540
```

-continued

```
tctatttgtc gtgcgtgcat gtgtccatgg tgtggtgggg ggcaggggtt ttcggggttg    600
cggttgaagg caccttatca gaaagatgcc ctcagagata gaggtagccc cctcccccg     660
atcttcgacc agtcctgtca ggcgaacact ttcacccgtc gttcacctcg ttacacacaa    720
ggagtagacc tctgaagttc taattgtcat aaatgcccct cccccctccc tctttccctt    780
gatcctcccc tccgagcaga ttatgaagac cttcaacatc tctcagcagg atctggagct    840
ggtggaggtc gccactgaga agatcaccat gctctatgag gacaacaagc accatgtcgg    900
ggcggccatc aggaccaaga ctggggagat catctctgct gtccacattg aggcctacat    960
tggcagggtc actgtctgtg ctgaagccat tgccattggg tctgctgtga gcaacgggca   1020
gaaggacttt gacaccattg tggctgtcag gcacccctac tctgatgagg tggacagatc   1080
catcagggtg gtcagcccct gtggcatgtg cagagagctc atctctgact atgctcctga   1140
ctgctttgtg ctcattgaga tgaatggcaa gctggtcaaa accaccattg aggaactcat   1200
cccctcaag tacaccagga actaagcttc tgtggaagag ccagtggtag tagcagtagc   1260
agcagcagta gcagccgcag cactcagtgt tggcgcgaga gattgtccat cccttcttaa   1320
cctaccggaa gagaaataag gcctttctcc cgtagctgtc ttcgtttgtt tgtgctgatt   1380
gcttgatatg agagtgttga attcctgcat catgtttttc tctgtagtcc tttcctaccc   1440
ccgtcatttt cttttctccc tggttcttct tttgtcaccc ttattttaca taaaattttc   1500
tttgtttata gtgagaggaa ggtagagagg ggaaaacaag aacaacgaac gcaagcgtgt   1560
gaaaggaggg cgagtagaag agaaacagat ctgttgagca ttgagagtgg agccggggga   1620
aaggcttgtg tgttgtcttt gaaaaagttg tttaaatcac gaatccgtta gttctcatgt   1680
gtacctcttt cactacatgt gatggagaaa acaaaagtgt gaggattaat tgaagaaaaa   1740
gaagagttcg acacgtcaaa ccgcccaaaa gacgtcacaa agagaacttg attctctttg   1800
ccgtgttgat cctgtctttt cccccagctt ttcttgccac ccgtggcaca cgagatggac   1860
aagatcag                                                           1868
```

VCP-BASED VECTORS FOR ALGAL CELL TRANSFORMATION

CROSS-REFERENCE TO RELATED APPLICATIONS

The present application claims the benefit and priority of U.S. Non-Provisional patent application Ser. No. 13/685,659 filed on Nov. 26, 2012, titled "VCP-Based Vectors for Algal Cell Transformation," which in turn claims the benefit and priority of U.S. Non-Provisional patent application Ser. No. 12/480,635 filed on Jun. 8, 2009, titled "VCP-Based Vectors for Algal Cell Transformation," which in turn claims the benefit and priority of U.S. Provisional Patent Application Ser. No. 61/059,672 filed on Jun. 6, 2008, titled "VCP-Based Vector for *Nannochloropsis* Transformation," all which are hereby incorporated by reference.

The present continuation application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

1. Field of the Invention

This invention relates to molecular biology, and more specifically, to the expression of exogenous DNA elements in algal cells.

2. Description of Related Art

Manipulating the DNA of a cell may confer upon the cell new abilities. In many cases, the genetic manipulation is carried out by introducing functional DNA that was prepared outside the cell using molecular techniques. For example, a transformed cell (i.e., a cell that has taken-up exogenous DNA) may be more robust than the wild-type cell. For many so-called model biological systems (i.e., well-studied organisms), the DNA elements for transformation have been developed. For other organisms, of which less is known, transformation is a major milestone that must be achieved to facilitate genetic engineering. Many algal species fall into the category of non-model organisms, with recalcitrant cell walls that make them notoriously difficult to transform. Accordingly, there is a need for an expression vectors for *Nannochloropsis* transformation.

SUMMARY OF THE INVENTION

Provided herein are exemplary vectors for transforming algal cells. In exemplary embodiments, the vector comprises a Violaxanthin-chlorophyll a binding protein (Vcp) promoter driving expression of an antibiotic resistance gene in an algal cell. Embodiments of the invention may be used to introduce a gene (or genes) into the alga *Nannochloropsis*, such that the gene(s) are expressed and functional. This unprecedented ability to transform *Nannochloropsis* with high efficiency makes possible new developments in phycology, aquaculture and biofuels applications.

BRIEF DESCRIPTION OF THE DRAWINGS

FIG. 4 shows an exemplary nucleotide sequence (SEQ ID NO:3) wherein the Sh ble gene of the PL90 vector was replaced with a gene conferring resistance against blasticidin.

DETAILED DESCRIPTION OF THE INVENTION

Transformed algae may be useful in aquaculture production. The transformation of small algal cells with tough membranes, however, is difficult to achieve. Embodiments of the present invention are useful in the efficient transformation of *Nannochloropsis*, a microalga of about 3-5 micrometers in size.

Various exemplary embodiments provided herein use a Violaxanthin-chlorophyll a binding protein (Vcp) promoter in a transformation construct to drive high levels of gene expression in algal cells at low light intensities. The transformation construct may be introduced within an algal cell or within an algal genome using one of the exemplary methods described in U.S. Non-Provisional patent application Ser. No. 12/480,611 filed on Jun. 8, 2009, titled "Transformation of Algal Cells," which is hereby incorporated by reference. An exemplary *Nannochloropsis* transformant in a logarithmic growth phase, plated onto F/2 media, and allowed to incubate at various light intensities for about two months, demonstrated that more transformant colonies could grow at high levels (about 25 ug/ml) of zeocine at low light levels. Thus, the Vcp promoter is active at lower light intensities, such that a transformation construct comprising a Vcp promoter may be useful in aquaculture ponds receiving less light, such as in the case of algae grown deep in a pond. Additionally, a Vcp promoter may be useful in modulating the expression of genes governed by the Vcp promoter, by varying the intensity of incident light.

Figure 1A:
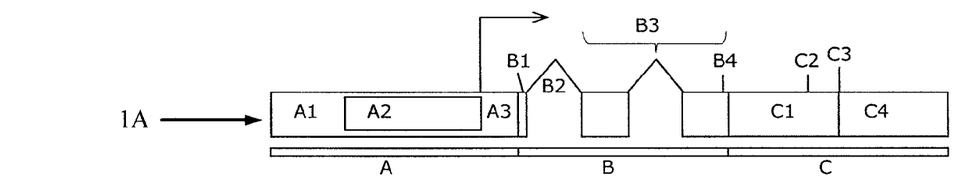
FIG. 1A shows a sequence of the genomic DNA of *Nannochloropsis oceanica*.

FIG. 1A shows the sequence genomic DNA of *Nannochloropsis oceanica*, which includes the Vcp gene and regulatory elements. Please note that for illustration purposes, 2 exons and 1 intron within B3 are illustrated. In fact, the gene harbors more than these components. The sequenced genomic DNA has the structure A-B-C, where B is the DNA encoding the Vcp gene (including introns), A is the DNA sequence in front of the Vcp gene, and C is the DNA sequence after the Vcp gene.

Sequence A includes the promoter which drives expression of the Vcp gene. The region from transcription start to translation start (the start ATG triplet) is the 5'-untranslated region A3. The sequence preceding the start methionine comprises A1, A2 and A3. The start methionine B1 is immediately followed by an intron B2 and the remaining exons and introns B3 of the Vcp gene. The Vcp gene ends with the stop codon B4. The sequence downstream of the Vcp gene (called C), includes the untranslated region C1, a polyadenylation signal C2, the stop of transcription C3 and downstream DNA sequence C4.

Figure 1B:
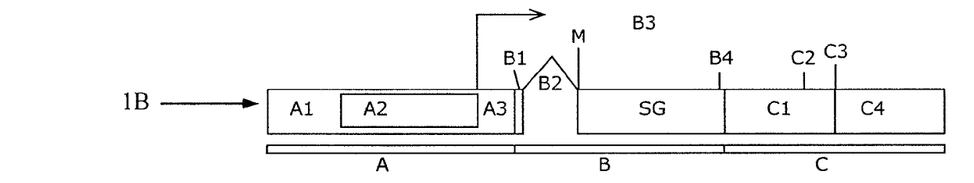
FIG. 1B shows an exemplary DNA transformation construct representing the functional insert of the PL90 vector.

FIG. 1B shows an exemplary DNA transformation construct representing the functional insert of the PL90 vector. Here, part B3 (FIG. 1A) was replaced with the reading frame of the Sh ble gene found in *Streptoalloteichus hindustanu*, yielding the PL90 vector as described herein.

FIG. 1B may also be used to show the structure of the various exemplary vector constructs PL90, H8 and B9 as described herein. The difference between the three exemplary vector constructs is the type of selection marker gene (SG) used: the Sh ble gene (PL90), the hygromycin B phosphotransferase gene (H8), or the blasticidin S deaminase (B9) gene.

Example One. We identified a Vcp (violaxanthine chlorophyll a binding protein) gene in a public nucleotide database (NCBI) for a *Nannochloropsis* strain (http://www.ncbi.nlm.nih.gov/nuccore/2734863). We constructed primers against this gene and recovered the genomic area in front of and behind the gene. We designed a DNA transformation construct replacing part B3 of the genome (FIG. 1A) with the reading frame of the Sh ble gene from *Streptoalloteichus hindustanus* (which confers resistance against the drug bleomycine), yielding the exemplary PL90 vector. This exemplary construct is illustrated in FIG. 1B.

We retained the start methionine of the Sh ble gene. We introduced a second start methionine immediately after the intron B2, thus the translation product includes spliced transcripts of the Sh ble gene with two consecutive methionines. The spliced transcript thus starts with the amino acids "MIM," with the second methionine being the beginning of the Sh ble gene. This exemplary construct was linearized within the vector by restriction digestion and used for the transformation of *Nannochloropsis oceanica*.

Figure 2:
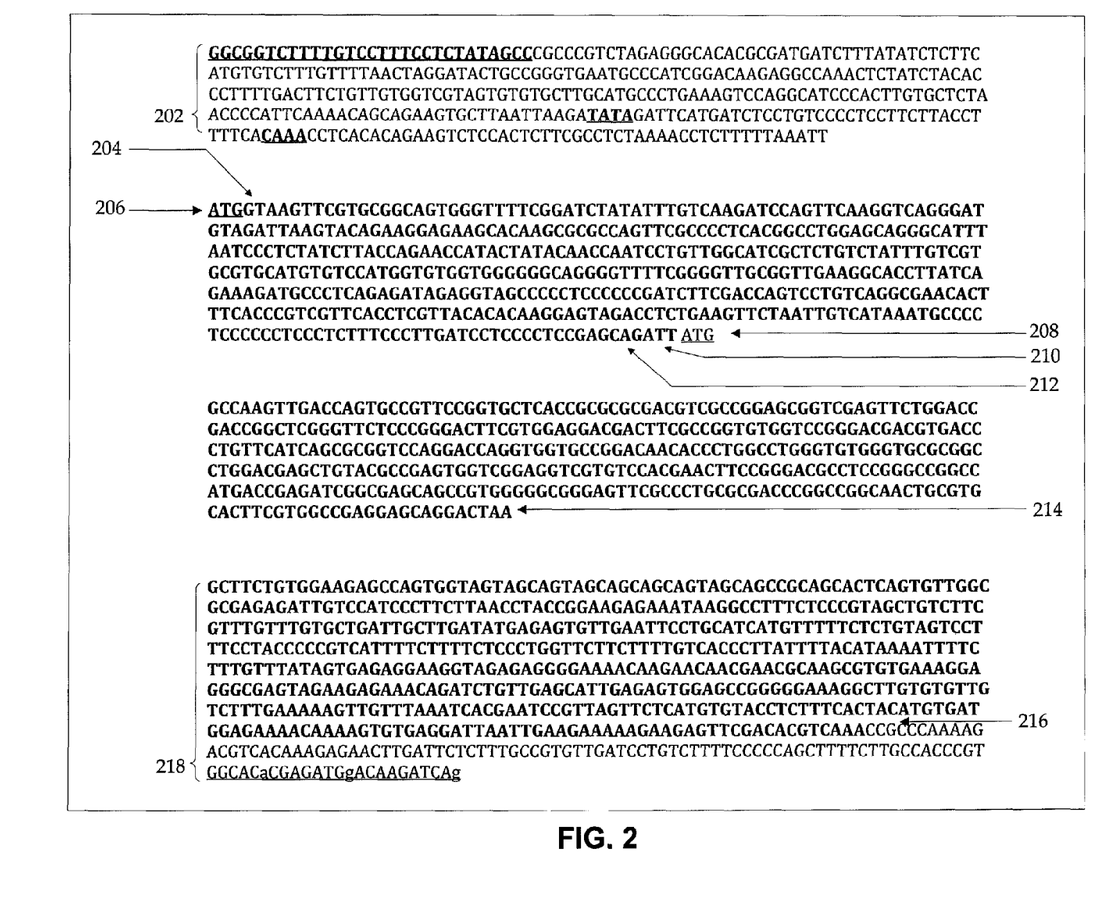
FIG. 2 shows an exemplary nucleotide sequence (SEQ ID NO:1) for the insert of the PL90 vector.

FIG. 2 shows an exemplary nucleotide sequence (SEQ ID NO:1) for the insert of the PL90 vector. 202 represents A from FIGS. 1A-1B, which is the DNA sequence in front of the Vcp gene. 204 represents the left intron border of the first Vcp intron. 206 represents the start methionine of the Vcp gene. 208 represents the beginning of the selection marker gene (i.e., the beginning of the Sh ble gene, ATG). 210 represents an introduced artificial sequence, TT. 212 represents the right intron border of the first Vcp intron. 214 represents the stop codon of the selection marker gene, TAA. 216 represents where polyadenylation occurs, after the CCGCCC sequence. 218 represents C from FIGS. 1A-1B, which is the DNA sequence downstream of the Vcp gene.

Figure 3:
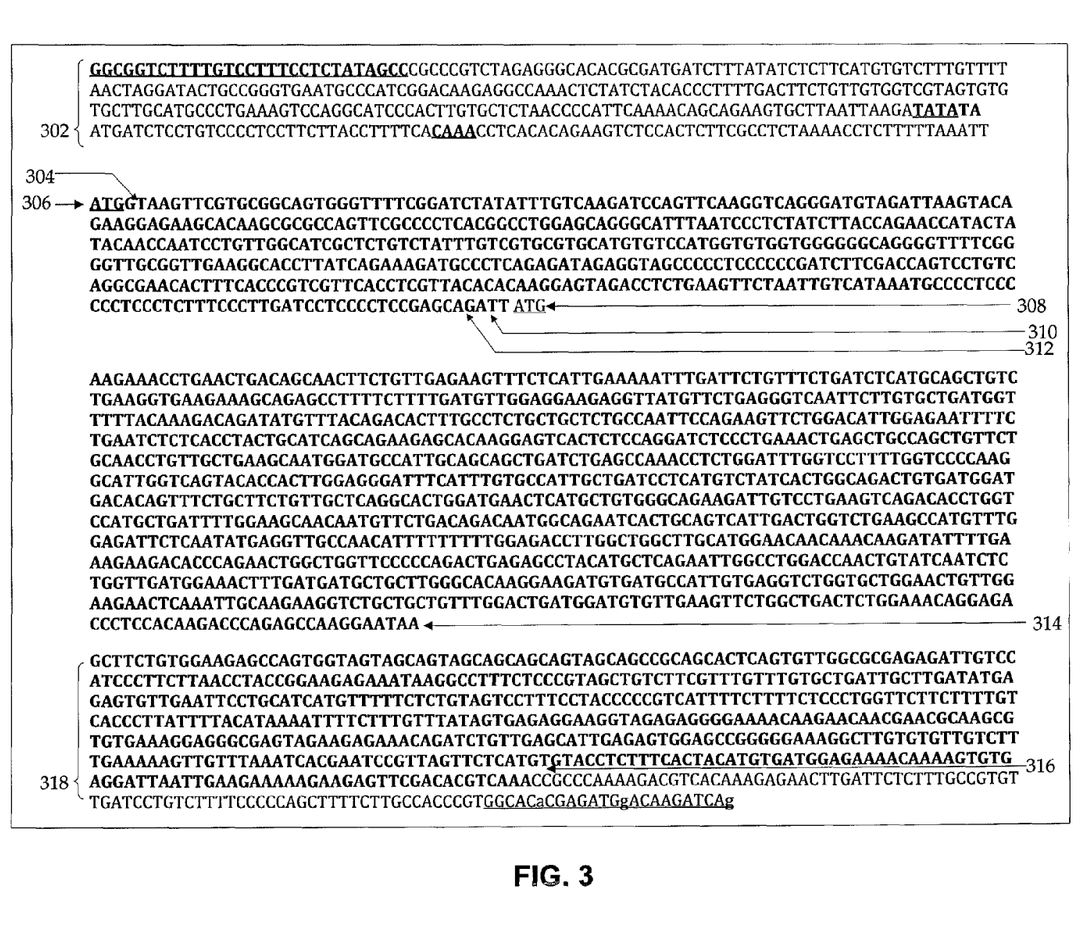
FIG. 3 shows an exemplary nucleotide sequence (SEQ ID NO:2) wherein the Sh ble gene of the PL90 vector was replaced with a gene conferring resistance against hygromycin B.

FIG. 3 shows an exemplary nucleotide sequence (SEQ ID NO:2) wherein the Sh ble gene of the PL90 vector was replaced with a gene conferring resistance against hygromycin B. 302 represents A from FIGS. 1A-1B, which is the DNA sequence in front of the Vcp gene. 304 represents the left intron border of the first Vcp intron. 306 represents the start methionine of the Vcp gene. 308 represents the beginning of the selection marker gene (i.e., the beginning of the hygromycin B phosphotransferase gene, ATG). 310 represents an introduced artificial sequence, TT. 312 represents the right intron border of the first Vcp intron. 314 represents the stop codon of the selection marker gene, TAA. 316 represents where polyadenylation occurs, after the CCGCCC sequence. 318 represents C from FIGS. 1A-1B, which is the DNA sequence downstream of the Vcp gene.

FIG. 4 shows an exemplary nucleotide sequence (SEQ ID NO:3) wherein the Sh ble gene of the PL90 vector was replaced with a gene conferring resistance against blasticidin. 402 represents A from FIGS. 1A-1B, which is the DNA sequence in front of the Vcp gene. 404 represents the left intron border of the first Vcp intron. 406 represents the start methionine of the Vcp gene. 408 represents the beginning of the selection marker gene (i.e., the beginning of the blasticidin-S deaminase gene, ATG). 410 represents an introduced artificial sequence, TT. 412 represents the right intron border of the first Vcp intron. 414 represents the stop codon of the selection marker gene, TAA. 416 represents where polyadenylation occurs, after the CCGCCC sequence. 418 represents C from FIGS. 1A-1B, which is the DNA sequence downstream of the Vcp gene.

The exemplary vectors PL90 (FIG. 2), H8 (FIG. 3) and B9 (FIG. 4) are useful for the transformation of *Nannochloropsis*. Selection occurred on 2 µg/ml zeocine (for vector PL90), 300 µg/ml hygromycin B (vector H8), or 50 50 µg/ml blasticidin S (vector B9).

Resistant colonies were only obtained when the appropriate vectors were used with the corresponding antibiotic. The success of transformation was checked and proofed via PCR on genomic DNA isolated from potential transformed colonies obtained by transformation with the Vcp based vectors described herein.

The Vcp promoter described herein drives expression of the Vcp of *Nannochloropsis*, a protein which is expressed in different levels at different physiological conditions. Algal cells acclimated to higher light intensities for example typically accumulate fewer light harvesting complexes than those acclimated to lower light intensities. We thus wanted to find out if the Vcp promoter described herein confers resistance to higher concentrations of zeocine (thus indicating higher expression levels of the Vcp promoter-driven Sh ble gene) in different light intensities. We thus transformed *Nannochloropsis* cells with the construct shown in FIG. 2 and allowed selection on agar plates in different light intensities. For this purpose, we plated a single transformation experiment on agar plates containing 25 µg/ml zeocine, or 25 µg/ml zeocine but the cells plated within top-agarose, or on agar plates containing no zeocine at all. Wild type (no Sh ble gene) was consistently killed completely at 2 µg/ml zeocine. Resistance to higher concentrations of zeocine (e.g. 25 µg/ml) indicates higher expression level of the selection gene Sh ble at lower irradiance levels.

Figure 5:
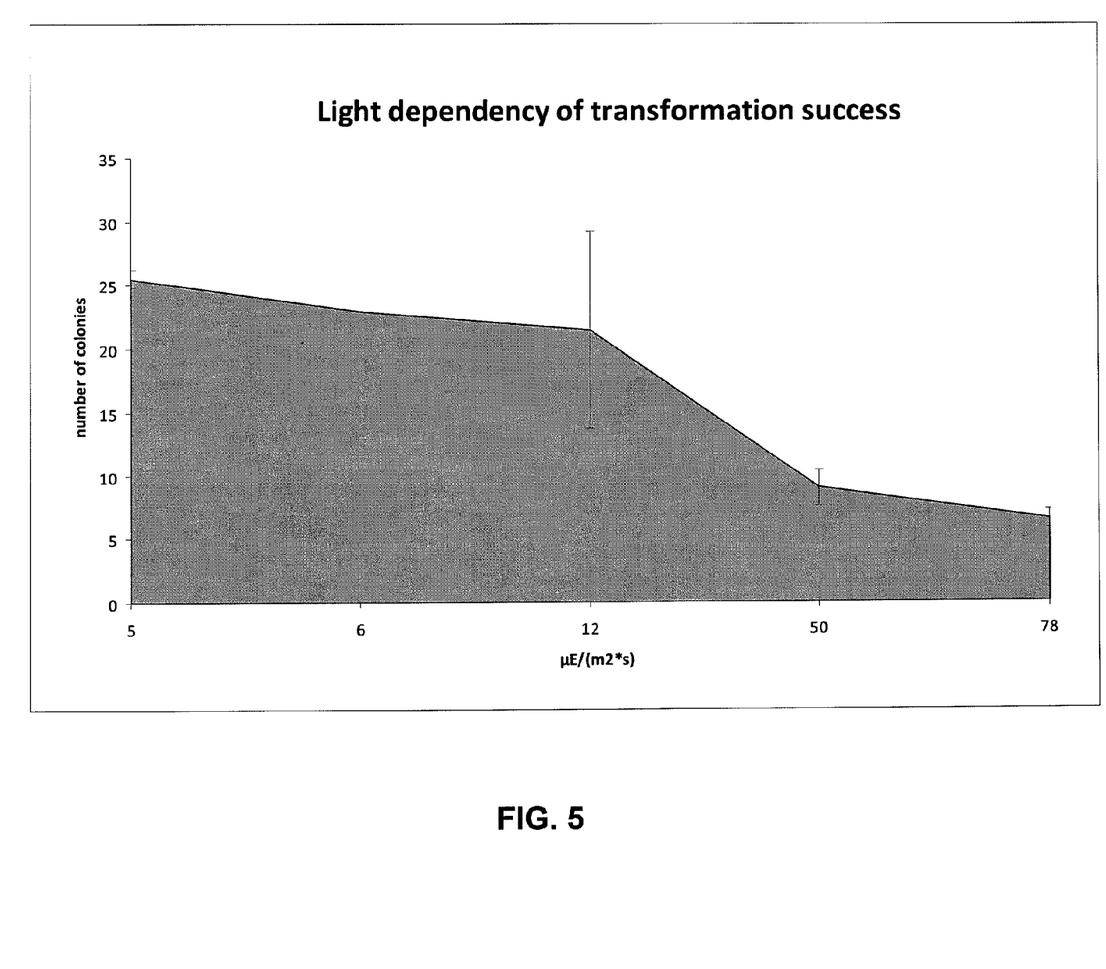
FIG. 5 shows the number of exemplary transformed algal cell colonies obtained when cells from a single transformation experiment have been plated under varying light conditions.

FIG. 5 shows the number of exemplary transformed algal cell colonies obtained when cells from a single transformation experiment have been plated under varying light conditions. FIG. 5 shows that the number of colonies (which is equal to the number of transformed cells which can stand concentrations of zeocine as high as 25 µg/ml) increases with decreasing light intensities. The highest number of transformants was obtained at low light intensities at 5 µE (µmol photons/(m2*s)). The result indicates that the exemplary construct utilized (as shown in FIG. 2) has a higher level of gene expression at lower light intensities than at higher light intensities. Accordingly, the exemplary constructs shown in FIGS. 2-4 might be utilized for the expression of genes modulated by the intensity of light.

Figure 6:
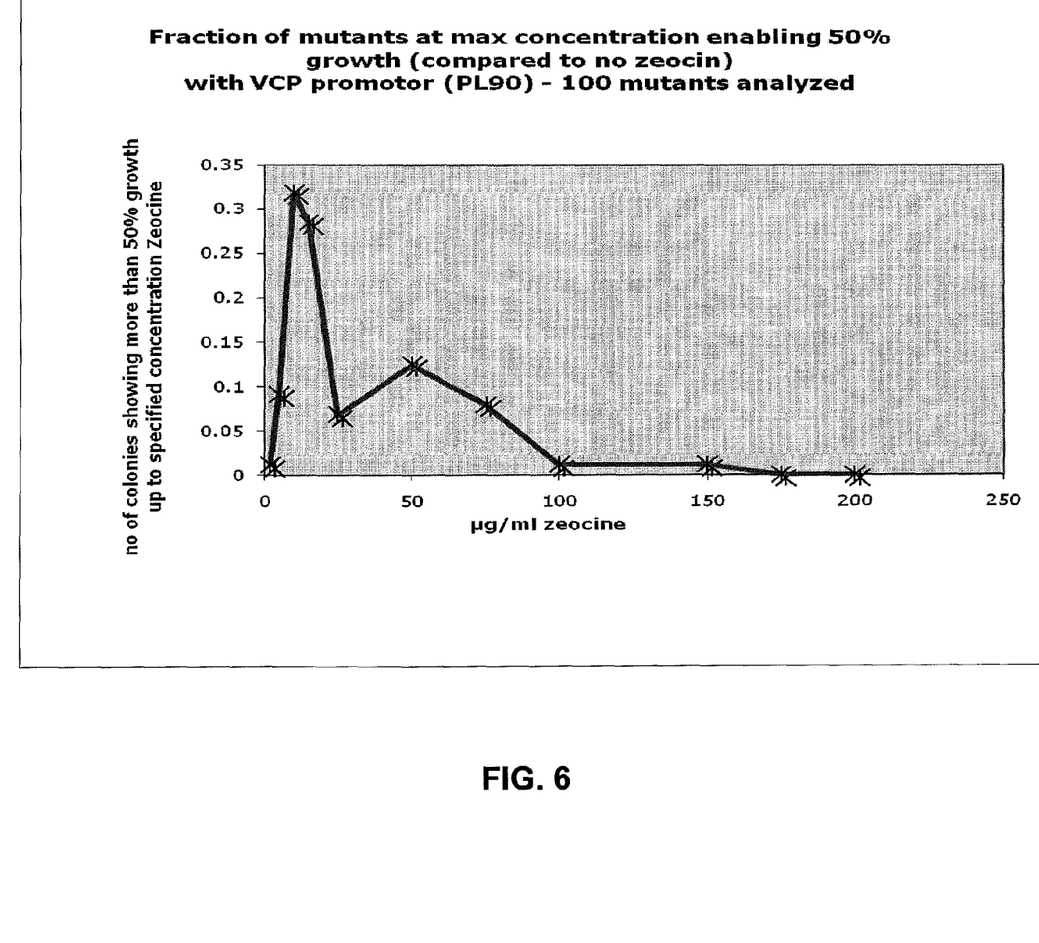
FIG. 6 shows the number of exemplary transformed algal mutants obtained under varying zeocine concentrations.

FIG. 6 shows the number of exemplary transformed algal mutants obtained and showing fifty percent (50%) or more growth at a given zeocine concentration but less than 50% at the next highest tested zeocine concentration. FIG. 6 illustrates the frequency of 96 clones obtained with the transformation vector PL90 showing more than 50% growth (in a liquid assay monitoring growth via OD750) at a certain zeocine concentration, but less than 50% at the next higher tested zeocine concentration.

Please note, wild-type cells and control cells (those transformed with pJet1 NOT containing a construct) never form colonies on zeocine concentrations 2 μg/ml or above, nor is there any detectable growth in liquid culture at such concentrations of zeocine. These results demonstrate that the Sh ble gene driven by the Vcp promoter in the construct confers resistance against zeocine concentrations up to 75 μg/ml, while wild-type cells consistently cannot survive concentrations above 2 μg/ml.

We subsequently replaced the reading frame of the Sh ble gene with genes conferring resistance to hygromycin B (transformation construct H8) and blastocidin (transformation construct B9) and used these vectors for transformation of *Nannochloropsis oceanica*. Again, we observed many transformation events (while the control did not show any colonies developing). Selection conditions were identical as for the PL90 transformation vector, with the exception that hygromycin B at 300 μg/ml or blastocidin S at 50 μg/ml were used.

Figure 7:
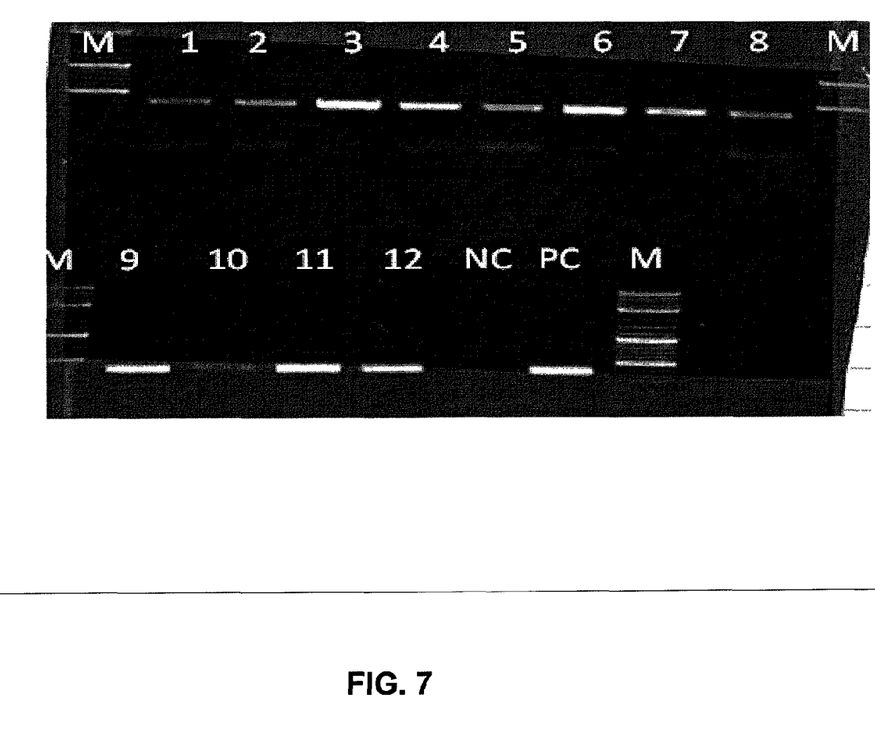
FIG. 7 shows the molecular analysis of exemplary transformed algal cells transformed with the PL90 vector and grown in the presence of zeocine.

FIG. 7 shows the molecular analysis of exemplary transformed algal cells transformed with the PL90 vector and grown in the presence of zeocine. 12 randomly picked colonies were derived from a transformation event with the vector PL90 and selection on zeocine (2 μg/ml). A control colony was obtained from a plate with wild-type colonies. Cells were resuspended in buffer (1× yellow tango buffer from Fermentas) and incubated with DNAse in order to digest possible residual extra cellular PL90 DNA used for the transformation event. The cells were then washed twice in seawater and resuspended in Millipore water and heated to 95° C. in order to bring the intracellular DNA into solution.

A standard PCR employing Sh ble gene primers (113 Sh ble for short ATG GCC AAG TTG ACC AGT GCC GT, 111 Sh ble rev short TTA GTC CTG CTC CTC GGC CAC GAA) utilizing a taq polymerase was performed on lysates of the 12 colonies obtained after transformation (colonies 1-12), of the control wild type colony without (negative control NC) or with (positive control PC) vector PL90 added.

The PCR reactions were separated on an ethidium bromide containing 1% agarose gel in TAE buffer. The 12 colonies from the transformation event contained the Sh ble gene (~375Nt), as does the positive control, but NOT the negative control. We conclude that that the Sh ble gene is contained within the cells and that the vector PL90 was used as a transformation construct to confer resistance against zeocine.

We then performed a Tail PCR (Liu and Hang 1998) employing the primers shown in the table below:

```
151 pJet1-prim
    CTTGCTGAAAAACTCGAGCCATCCG 152 pJet1-sec
    Atggtgttcaggcacaagtgttaaagc 153 pJet1-tert
    Ggtttagaacttactcacagcgtgatgc
```

The primers shown above correspond to the region on the pJet1 vector right after the linearization restriction site. Note that the constructs PL90, H8 and B9 are within the vector pJet1. We recovered an approximately 400 base pair long fragment which we sequenced. The sequence is shown in FIG. 8.

Figure 8:
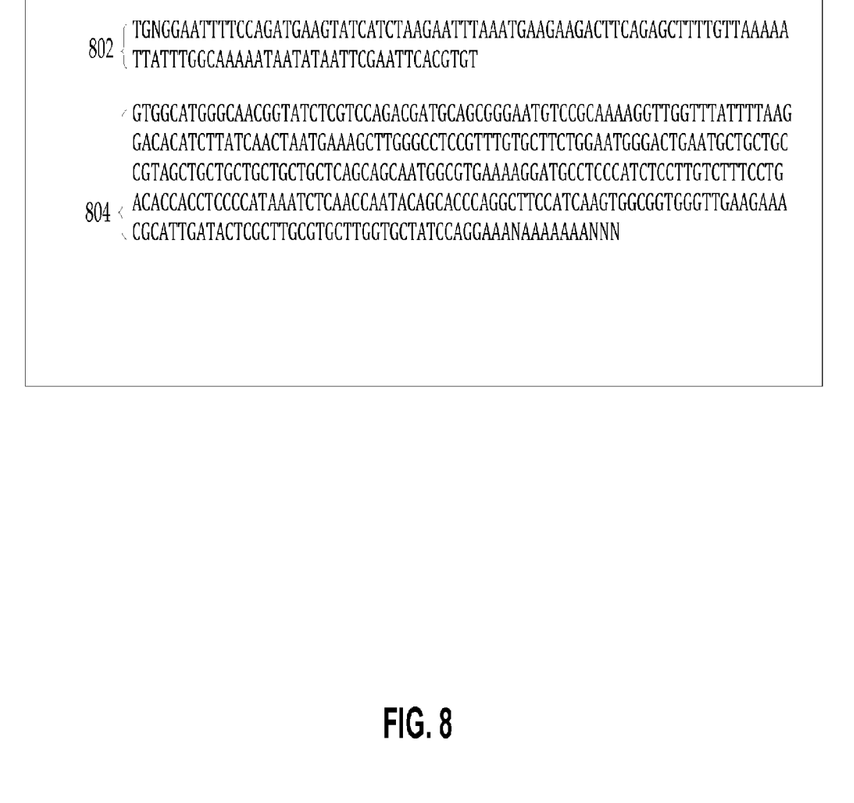
FIG. 8 shows an approximately 400 base pair fragment that indicates the exemplary linearized PL90 vector is stably integrated within the genome of *Nannochloropsis oceanica*.

FIG. 8 shows an approximately 400 base pair fragment that indicates the exemplary linearized PL90 vector is stably integrated within the genome of *Nannochloropsis oceanica*. We thus conclude that the exemplary vectors presented herein successfully drive expression of genes in *Nannochloropsis oceanica*.

While various embodiments have been described above, it should be understood that they have been presented by way of example only, and not limitation. Thus, the breadth and scope of a preferred embodiment should not be limited by any of the above-described exemplary embodiments.

What is claimed is:

1. An expression vector for algal cell transformation comprising the nucleotide sequence of SEQ ID NO:3.

2. The expression vector of claim 1, wherein a promoter in the expression vector modulates the expression of a gene governed by the promoter in response to light intensity.

3. The expression vector of claim 2, wherein the promoter in the expression vector increases the expression of the gene governed by the promoter in response to a decrease in light intensity.

4. The expression vector of claim 2, wherein the promoter is a Vcp promoter.

5. The expression vector of claim 1, wherein the algal cell is of algal genus *Nannochloropsis*.

6. The expression vector of claim 1, wherein the expression vector is at least partially expressed as part of a transformed algal cell.

\* \* \* \* \*

UNITED STATES PATENT AND TRADEMARK OFFICE
CERTIFICATE OF CORRECTION

| | | |
|---|---|---|
| PATENT NO. | : 8,753,879 B2 | Page 1 of 1 |
| APPLICATION NO. | : 13/915555 | |
| DATED | : June 17, 2014 | |
| INVENTOR(S) | : Oliver Kilian et al. | |

It is certified that error appears in the above-identified patent and that said Letters Patent is hereby corrected as shown below:

On the title page, item (73)
Assignee's name should be: "Aurora Algae, Inc."

Signed and Sealed this
Thirtieth Day of September, 2014

Michelle K. Lee
*Deputy Director of the United States Patent and Trademark Office*